United States Patent
Iijima

(10) Patent No.: US 9,873,642 B2
(45) Date of Patent: *Jan. 23, 2018

(54) SYSTEM AND METHOD FOR PRODUCING GASOLINE

(71) Applicant: MITSUBISHI HEAVY INDUSTRIES, LTD., Tokyo (JP)

(72) Inventor: Masaki Iijima, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 530 days.

This patent is subject to a terminal disclaimer.

(21) Appl. No.: 14/368,151

(22) PCT Filed: Dec. 13, 2012

(86) PCT No.: PCT/JP2012/082327
§ 371 (c)(1),
(2) Date: Jun. 23, 2014

(87) PCT Pub. No.: WO2013/108525
PCT Pub. Date: Jul. 25, 2013

(65) Prior Publication Data
US 2015/0005557 A1 Jan. 1, 2015

(30) Foreign Application Priority Data
Jan. 17, 2012 (JP) ................................. 2012-007215

(51) Int. Cl.
*B01J 8/04* (2006.01)
*B01J 8/06* (2006.01)
(Continued)

(52) U.S. Cl.
CPC .................... *C07C 1/22* (2013.01);
*B01J 8/04* (2013.01); *B01J 8/06* (2013.01);
*B01J 8/067* (2013.01);
(Continued)

(58) Field of Classification Search
USPC ................................................. 422/621, 629
See application file for complete search history.

(56) References Cited

U.S. PATENT DOCUMENTS 4,048,250 A * 9/1977 Garwood ............ C07C 29/1518
518/704
4,404,414 A * 9/1983 Penick ...................... C07C 1/20
585/315

(Continued)

FOREIGN PATENT DOCUMENTS

DE    10 2009 046 790 A1    5/2011
EA          004130 B1    12/2003
(Continued)

OTHER PUBLICATIONS

International Search Report dated Feb. 26, 2013 issued in corresponding application No. PCT/JP2012/082327.
(Continued)

*Primary Examiner* — Jennifer A Leung
(74) *Attorney, Agent, or Firm* — Westerman, Hattori, Daniels & Adrian, LLP

(57) ABSTRACT

A system or method for producing gasoline from natural gas via methanol can effectively use the heat of reaction generated during the synthesis of gasoline and is capable of readily cooling the gasoline synthesis column in the production of gasoline from natural gas via methanol. A steam reformer 10 steam-reforms natural gas to generate reformed gas, methanol is synthesized by a methanol synthesis column 20 from the reformed gas, and in synthesizing gasoline from methanol by using a gasoline synthesis column 30, combustion air 41 to be supplied to the steam reformer 10 is preheated with the heat of reaction generated in the gasoline synthesis column 30, and then the preheated combustion air 41 is supplied to the steam reformer 10.

2 Claims, 3 Drawing Sheets

(51) Int. Cl.
  *C07C 1/22*   (2006.01)
  *C10L 1/06*   (2006.01)
  *C01B 3/38*   (2006.01)
  *C07C 29/151*   (2006.01)
  *C07C 41/09*   (2006.01)
  *C07C 1/02*   (2006.01)
  *C07C 1/20*   (2006.01)

(52) U.S. Cl.
  CPC ............ *C01B 3/384* (2013.01); *C07C 29/151* (2013.01); *C07C 29/1518* (2013.01); *C07C 41/09* (2013.01); *C10L 1/06* (2013.01); *C01B 2203/0233* (2013.01); *C01B 2203/0283* (2013.01); *C01B 2203/061* (2013.01); *C01B 2203/062* (2013.01); *C01B 2203/0811* (2013.01); *C01B 2203/0827* (2013.01); *C01B 2203/1058* (2013.01); *C01B 2203/1241* (2013.01); *Y02P 20/129* (2015.11); *Y02P 30/20* (2015.11)

(56) References Cited

U.S. PATENT DOCUMENTS

| | | | |
|---|---|---|---|
| 4,523,046 | A | 6/1985 | Gould et al. |
| 4,814,535 | A | 3/1989 | Yurchak |
| 4,894,394 | A * | 1/1990 | Van Dijk .............. C07C 29/156 518/700 |
| 5,602,289 | A | 2/1997 | van Dijk |
| 6,218,439 | B1 | 4/2001 | Kobayashi et al. |
| 9,284,234 | B2 * | 3/2016 | Iijima ....................... C10L 1/06 |
| 2010/0036186 | A1 | 2/2010 | Joensen et al. |

FOREIGN PATENT DOCUMENTS

| | | |
|---|---|---|
| EP | 1 277 697 A2 | 1/2003 |
| JP | 4-51596 B2 | 8/1992 |
| JP | 10-506668 A | 6/1998 |
| JP | 2002-338206 A | 11/2002 |
| JP | 2010-512435 A | 4/2010 |
| JP | 2013-112769 A | 6/2013 |
| RU | 2 204 527 C2 | 5/2003 |
| WO | 2011/155962 A1 | 12/2011 |

OTHER PUBLICATIONS

Honda, "GTG (Gas-To-Gasoline) Project starts running in New Zealand", Petrotech, Nov. 1, 1986, vol. 9, No. 11, pp. 986-991, with Concise Explanation of Relevance.

Office Action dated Dec. 4, 2015, issued in counterpart Japanese Patent Application No. 2012-007215, with English translation. (8 pages).

Notification of Transmittal of Translation of the International Preliminary Report on Patentability (Form PCT/IB/338) of International Application No. PCT/JP2012/082327 dated Jul. 31, 2014 with Forms PCT/IB373 and PCT/ISA/237.

Extended European Search Report dated Sep. 11, 2015, issued in counterpart European Patent Application No. 12865806.9 (7 pages).

Notice of Allowance dated Sep. 24, 2015, issued in counterpart Russian Patent Application No. 2014129050 (9 pages) with concise explanation of the Notice of Allowance.

Notice of Allowance dated Apr. 18, 2016, issued in counterpart Australian Patent Application No. 2012366429 (28 pages).

Notice of Acceptance dated Nov. 9, 2016, issued in counterpart Canadian Patent Application No. 2,862,794. (1 page).

* cited by examiner

SYSTEM AND METHOD FOR PRODUCING GASOLINE

TECHNICAL FIELD

The present invention relates to a system and a method for producing gasoline, and more specifically, relates to a system and a method for producing gasoline from natural gas via methanol.

BACKGROUND ART

In synthesizing methanol from natural gas, in most cases, natural gas is steam-reformed, then reformed gas containing hydrogen and carbon monoxide is generated, and methanol is then synthesized from the reformed gas. Furthermore, Japanese Patent Publication (B2) No. H04-51596 discloses a method for synthesizing gasoline from methanol via dimethyl ether (DME). The reaction for synthesizing gasoline from methanol is an exothermic reaction, and the reaction is run at a temperature of about 400° C.; however, the heat of such a high temperature has not been effectively used in conventional techniques.

In addition, because heat of reaction as high as about 400° C. is generated by synthesizing gasoline, it is necessary to cool a gasoline synthesis column. Japanese Patent Publication (B2) No. H04-51596 discloses a method in which heating and cooling are repeatedly carried out by using two stages of gasoline synthesis columns in order to perform the above-described cooling.

BACKGROUND LITERATURE

Patent Literature

Patent Literature 1: Japanese Patent Publication (B2) No. H04-51596

DISCLOSURE OF INVENTION

Problem to be Solved by Invention

In order to effectively use the heat of reaction generated during the synthesis of gasoline, a method may be used in which heat is recovered by generating steam by using the heat of reaction. However, considering that the heat of reaction generated during the synthesis of gasoline is as high as about 400° C. and that the critical point of water is at a temperature of 374° C. and a pressure of 218 atmospheres, there may be a problem in that it is very difficult to maintain the heat of reaction temperature at a specific level as high as about 400° C. by heat recovery carried out by using steam.

In addition, it is necessary to cool the gasoline synthesis column to a specific level and maintain its temperature; however, in the method disclosed in Japanese Patent Publication (B2) No. H04-51596 which uses multiple stages of gasoline synthesis columns, problems arise such that the total size of the device may become very large and the device configuration may become complex in order to lower the device temperature to a specific level and maintain it.

In order to solve the above-described problems, the purpose of the invention is to provide a system or a method configured to produce gasoline from natural gas via methanol, which, in producing gasoline from natural gas via methanol, effectively uses the heat of reaction generated during the synthesis of gasoline and is capable of readily cooling the gasoline synthesis column to a specific temperature.

Means for Solving the Problem

According to an aspect of the invention, a system for producing gasoline from natural gas via methanol includes a steam-reforming device for generating reformed gas by steam-reforming natural gas, a methanol synthesis device for synthesizing methanol from the reformed gas generated by the steam reforming device, a gasoline synthesis device for synthesizing gasoline from methanol synthesized by the methanol synthesis device, and an air preheating device for preheating combustion air to be supplied to the steam-reforming device by using the gasoline synthesis device.

The gasoline synthesis device may include at least two gasoline synthesis columns and a heat exchanger for carrying out heat exchange between the gasoline synthesized by the first gasoline synthesis column of the at least two gasoline synthesis columns and the methanol to be supplied to the first gasoline synthesis column. The second gasoline synthesis column of the at least two gasoline synthesis columns may be cooled with the gasoline that has been cooled by the heat exchanger.

The gasoline synthesis device may preferably include reaction tubes for running reactions of synthesizing gasoline from methanol and ducts which allow air to flow outside the reaction tubes, and may preferably carry out heat exchange between the synthesis heat generated inside the reaction tubes and air which flows through the ducts. In addition, two types of catalysts including a dimethyl ether synthesis catalyst for synthesizing dimethyl ether from methanol and a gasoline synthesis catalyst for synthesizing gasoline from the synthesized dimethyl ether may preferably be charged inside the reaction tubes in two stages. The ducts may preferably be configured so as to allow the air to flow outside the portion of the reaction tubes in which the dimethyl ether synthesis catalyst is charged and then flow outside the portion of the reaction tubes in which the gasoline synthesis catalyst is charged.

According to another aspect of the present invention, a method for producing gasoline from natural gas via methanol includes a steam-reforming step of generating reformed gas by steam-reforming natural gas, a methanol synthesis step of synthesizing methanol from the reformed gas generated in the steam-reforming step, a gasoline synthesis step of synthesizing gasoline from methanol synthesized in the methanol synthesis step, and an air preheating step of preheating combustion air to be supplied to the steam-reforming step with synthesis heat generated in the synthesis of gasoline.

At least two of the gasoline synthesis steps may be serially performed, and the method may include a step of carrying out heat exchange between gasoline synthesized by a first gasoline synthesis step of the at least two gasoline synthesis steps and methanol to be supplied to the first gasoline synthesis step. In addition, synthesis heat generated in a second gasoline synthesis step of the at least two gasoline synthesis steps may be cooled with the gasoline cooled by the heat exchanging step.

Advantageous Effects of Invention

As described above, according to the present invention, combustion air to be supplied for the steam-reforming of natural gas is preheated with synthesis heat generated in the synthesis of gasoline from methanol, and thereby heat of reaction generated by the synthesis of gasoline can be more effectively used and also the heat generated in the synthesis of gasoline can be more readily cooled compared with the case of heat recovery which uses steam.

DESCRIPTION OF EMBODIMENTS

Hereinbelow, an embodiment of a system and a method for producing gasoline from natural gas via methanol according to the present invention will be described with reference to the attached drawings.

Figure 1:
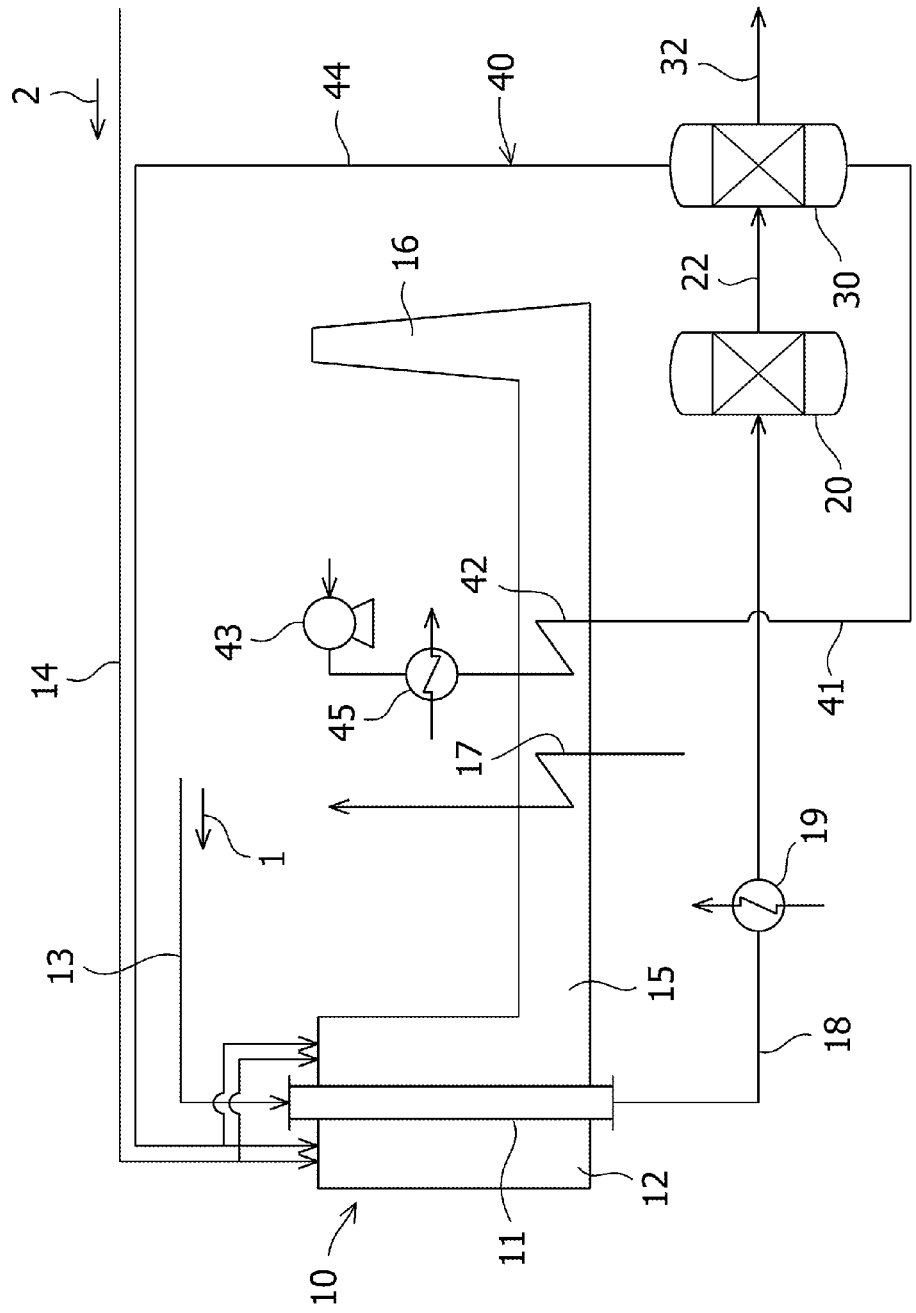
FIG. 1 is a schematic view showing an embodiment of a system for producing gasoline from natural gas via methanol according to the present invention.

As shown in FIG. 1, the system of the present embodiment includes a steam reformer 10, which is configured to generate reformed gas by steam-reforming natural gas, a methanol synthesis column 20, which is configured to synthesize methanol from the reformed gas generated by the steam reformer, a gasoline synthesis column 30, which is configured to synthesize gasoline from the methanol synthesized by the methanol synthesis column, and an air preheating device 40, which is configured to preheat combustion air to be supplied to a burning portion of the steam reformer.

The steam reformer 10 primarily includes a reaction tube 11 for steam reforming, a burning portion 12 disposed around the reaction tube 11, a waste heat recovery portion 15, which is configured to recover waste heat of the flue gas generated in the burning portion 12, and a stack 16, which is configured to release the flue gas to the atmosphere after waste heat has been recovered therefrom. The reaction tube 11, which includes a steam reforming catalyst charged inside the tube, is a device for generating hydrogen, carbon monoxide, and carbon dioxide from natural gas containing methane as its main ingredient by carrying out the following reactions. For the steam reforming catalyst, known catalysts such as a nickel-based catalyst can be used, for example.

$$CH_4 + H_2O \rightarrow 3H_2 + CO \qquad (1)$$

$$CO + H_2O \rightarrow H_2 + CO_2 \qquad (2)$$

A material supply line 13 for supplying a material 1, which includes natural gas and steam, is connected to an inlet of the reaction tube 11. The burning portion 12 includes a combustion burner (not shown) for heating the reaction tube 11, and a fuel supply line 14 for supplying a fuel 2 such as natural gas is connected to the combustion burner. A reformed gas supply line 18 is connected to an outlet of the reaction tube 11, which is a line for supplying reformed gas containing hydrogen, carbon monoxide, and carbon dioxide generated by the steam reforming reaction as its main ingredients to a methanol synthesis column 20.

The methanol synthesis column 20 is a device configured to synthesize methanol from reformed gas by running the following reactions.

$$CO + 2H_2 \rightarrow CH_3OH \qquad (3)$$

$$CO_2 + 3H_2 \rightarrow CH_3OH + H_2O \qquad (4)$$

The methanol synthesis column 20 includes a methanol synthesis catalyst charged inside the tube. For the methanol synthesis catalyst, known catalysts such as a copper-based catalyst can be used. A methanol supply line 22 is connected to methanol synthesis column 20, which is a line for supplying methanol synthesized by the methanol synthesis column 20 to the gasoline synthesis column 30. Note that in addition to the synthesized methanol, liquid crude methanol containing water, which is a byproduct of the reaction of Formula (4), flows in the methanol supply line 22.

The gasoline synthesis column 30 is a device which is configured to synthesize gasoline from methanol by running the reactions of the following Formulae.

$$2CH_3OH \rightarrow CH_3OCH_3 + H_2O \qquad (5)$$

$$1/2nCH_3OCH_3 \rightarrow (CH_2)n + 1/2nH_2O \qquad (6)$$

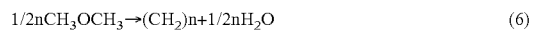

As described above, methanol is synthesized by the gasoline synthesis reaction expressed in Formula (3) into gasoline via the dimethyl ether (DME) synthesis reaction expressed by Formula (5). In the gasoline synthesis column 30, two types of catalysts including the DME synthesis catalyst and the gasoline synthesis catalyst are provided in two stages so that two reactions can be run in stages. For the DME synthesis catalyst, known catalysts such as an aluminosilicate type zeolite-based catalyst can be used, for example. In addition, for the gasoline synthesis catalyst also, known catalysts such as an aluminosilicate type zeolite-based catalyst can be used.

A gasoline supply line 32 is connected with the gasoline synthesis column 30, which is a line for supplying gasoline synthesized by the gasoline synthesis column 30 to storage facilities (not shown).

The air preheating device 40 includes a fan 43 for feeding combustion air, a steam-combustion air heat exchanger 45 configured to preheat the combustion air with steam, a flue gas-combustion air heat exchanger 42, which is configured to further preheat combustion air with the flue gas that flows in the waste heat recovery portion 15 of the steam reformer 10, a combustion air introduction line 41 for introducing the preheated combustion air into the gasoline synthesis column 30 with the synthesis heat generated in the gasoline synthesis column 30 in order to further heat the preheated combustion air, and a combustion air supply line 44 for supplying the combustion air heated with the synthesis heat to the burning portion 12 of the steam reformer 10.

Figure 2:
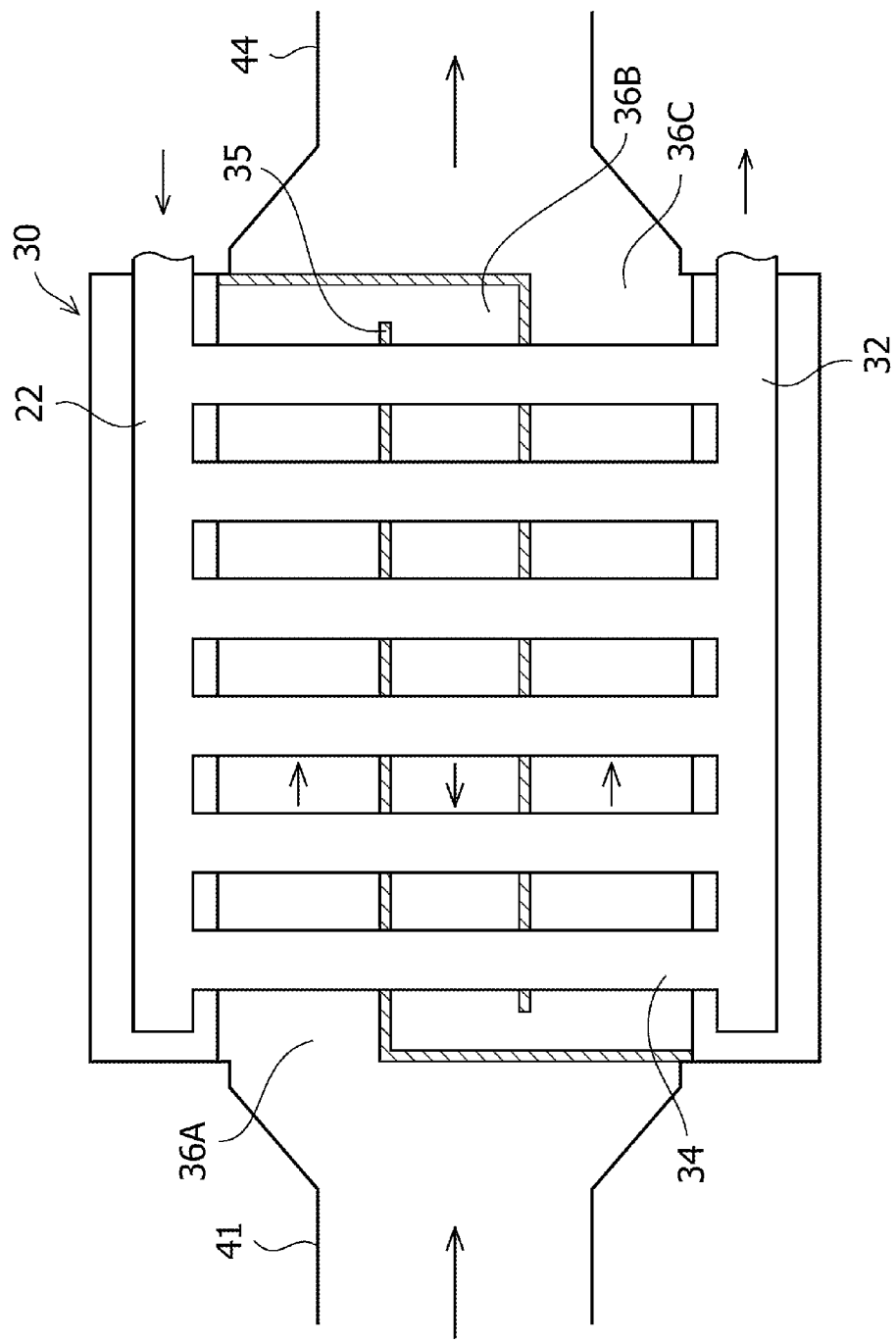
FIG. 2 is a schematic view showing an embodiment of a configuration of the gasoline synthesis column illustrated in FIG. 1.

Means for heating combustion air with the heat of reaction generated in the gasoline synthesis column 30 is not limited to specific means, but for example, the combustion air can be heated with steam obtained by heating boiler water with the heat of reaction generated in the gasoline synthesis column 30. Alternatively, as shown in FIG. 2, heat can be exchanged between the DME synthesis catalyst in the gasoline synthesis column 30 or the reaction tube charged with the gasoline synthesis catalyst and the combustion air. FIG. 2 will be described below.

The flue gas-combustion air heat exchanger 42 is disposed on the flue gas downstream side of the flue gas-steam heat exchanger 17 in the waste heat recovery portion 15 of the steam reformer 10. In other words, the waste heat recovery portion 15 of the steam reformer 10 includes the flue gas-steam heat exchanger 17 and the flue gas-combustion air heat exchanger 42 disposed in order of the flow of the flue gas from the burning portion 12 to the stack 16. The flue gas-steam heat exchanger 17 is a device for obtaining steam or heat to be used within the system, and is configured to recover heat from the flue gas and obtain high-pressure steam by heating boiler water and the like with the flue gas flowing inside the waste heat recovery portion 15.

Similarly, the reformed gas supply line 18 is provided with a reformed gas-steam heat exchanger 19, which is provided in order to obtain steam or heat to be used within the system. The reformed gas-steam heat exchanger 19 is a device configured to obtain high-pressure steam and recover heat from the reformed gas by heating boiler water and the like by using the reformed gas.

According to the above-described configuration, the fuel 2 such as natural gas is first supplied to the burning portion 12 of the steam reformer 10 via the fuel supply line 14. In the burning portion 12, the fuel 2 is burned together with air, and the reaction tube 11 is heated to a temperature ranging from about 800° C. to about 900° C.

After boiler water or the like is heated by the flue gas-steam heat exchanger 17 of the waste heat recovery portion 15 to recover heat, the flue gas containing carbon dioxide generated in the burning portion 12, which has the temperature of about 1,000° C., is cooled to a temperature ranging from about 300° C. to about 400° C. Then, after the combustion air from the fan 43 is heated by the flue gas-combustion air heat exchanger 42, the flue gas is released from the stack 16. Note that the combustion air supplied from the fan 43 is heated by the steam-combustion air heat exchanger 45 to a temperature ranging from about 60° C. to about 80° C.

On the other hand, the material 1 containing natural gas and steam is supplied to the reaction tube 11 of the steam reformer 10 via the material supply line 13. In the reaction tube 11 of the steam reformer 10, the material 1 is converted by a steam reforming reaction into reformed gas containing hydrogen, carbon monoxide, and carbon dioxide as its main ingredients by running the reaction of Formulae (1) and (2) described above. After heat is recovered by heating boiled water or the like by using the reformed gas-steam heat exchanger 19, the reformed gas is supplied to the methanol synthesis column 20 via the reformed gas feed line 18.

In the methanol synthesis column 20, methanol is synthesized from the reformed gas by running the reactions of Formulae (3) and (4). The methanol synthesis reactions are exothermic. The temperature of the reformed gas is controlled by the reformed gas-steam heat exchanger 19 to the range of about 160° C. to about 200° C., which is suitable for synthesis of methanol. Methanol synthesized by the methanol synthesis column 20 is supplied to the gasoline synthesis column 30 via the methanol supply line 22 as crude methanol containing water.

In the gasoline synthesis column 30, gasoline is synthesized from methanol by the reactions of Formulae (5) and (6). The synthesis reaction from methanol to DME run in the gasoline synthesis column 30 is an exothermic reaction, and its heat of reaction is 185 kcal equivalent to 1 kg of methanol. In addition, the gasoline synthesis reaction is also an exothermic reaction, and its heat of reaction is 231 kcal equivalent to 1 kg of methanol. Therefore, in synthesizing gasoline from methanol, the heat of reaction is 416 kcal equivalent to 1 kg of methanol. The combustion air introduced from the combustion air inlet line 41 is heated by using this heat of reaction.

Note that because water is generated in the reaction of Formula (6) as a byproduct, the crude methanol may contain water, and it is therefore not necessary to provide the methanol supply line 22 for supplying methanol to the gasoline synthesis column 30 with a purification device for removing water by distilling crude methanol, which is necessary in a conventional methanol synthesis plant.

With respect to the condition of the DME synthesis reaction performed by the gasoline synthesis column 30, it is preferable that the temperature range from 250° C. to 300° C. In addition, for the condition of the gasoline synthesis reaction, it is preferable that the temperature range from f 380° C. to 450° C. Therefore, the combustion air can be heated up to the range of about 300° C. to about 380° C.

The combustion air heated by the gasoline synthesis column 30 is supplied to the burning portion 13 of the steam reformer 10 via the combustion air supply line 44 together with the fuel 2. Because the combustion air is heated as described above, the supply of the fuel 2 to the burning portion 13 can be reduced.

In the present embodiment, as described above and differently from conventional methanol synthesis plants, the gasoline synthesis column 30 is provided in which exothermic reactions are run and thermal energy is generated, and in addition, the combustion air in the steam reformer 10 is preheated by using the exothermic energy generated in the gasoline synthesis column 30, and thereby the amount of supply of the fuel 2 to the steam reformer 10 can be reduced.

The detailed configuration of the gasoline synthesis column 30 will be described below with reference to FIG. 2. As shown in FIG. 2, the gasoline synthesis column 30 includes a reaction tube 34 for producing gasoline from methanol, and a duct 36, in which the combustion air heated through the reaction tube 34 flows. A plurality of reaction tubes 34 is disposed in parallel to one another in the inside of the gasoline synthesis column 30. One end of the respective reaction tubes 34 is connected with the methanol supply line 22 so as to feed methanol, which is the material. In addition, the other end of the respective reaction tubes is connected with the gasoline supply line 32 so as to discharge gasoline, which is the product.

Each reaction tube 34 includes a catalyst (not shown) charged inside the tube. For the catalyst, two types of catalysts including a DME synthesis catalyst and a gasoline synthesis catalyst are charged in two stages. The DME synthesis catalyst is charged into the respective reaction tubes 34 on the side of the methanol supply line 22 and the gasoline synthesis catalyst is charged into the respective reaction tube 34 on the side of the gasoline supply line 32.

Inside the gasoline synthesis column 30, the duct 36 which allows the combustion air to flow outside the reaction tubes 34 is formed. One end of the duct 36 is connected to the combustion air inlet line 41 in order to supply combustion air. In addition, the other end is connected to the combustion air supply line 44 to discharge combustion air. The material of the reaction tubes 34 may be a material capable of heating the air flowing outside the reaction tubes 34 via the tube wall and is not limited to a specific type, and preferable examples thereof include metal materials such as steel, chromium-nickel steel, stainless steel, etc.

The duct 36 is configured so that the combustion air flows in the direction perpendicular to the longitudinal direction of the reaction tubes 34. In addition, the duct 36 is also configured so as to be bent by a partitioning member 35 inside the gasoline synthesis column 30 so that the combustion air flows on the side of the methanol supply line 22 of the reaction tubes 34 on the inlet side of the duct, i.e., on the side of the combustion air inlet line 41, and so that the combustion air flows on the side of the gasoline supply line 32 of the reaction tubes 34 on the outlet side of the duct, i.e., on the side of the combustion air supply line 44. For example, as shown in FIG. 2, the partitioning member 35 provides two bending portions so that the duct 36 inside the gasoline synthesis column 30 is provided with a first duct 36A located on the side of the methanol supply line 22, a second duct 36B located in the center portion, and a third duct 36C located on the side of the gasoline supply line 32.

According to the above-described configuration, methanol is supplied from the methanol supply line 22 to the respective reaction tubes 34, and first, DME is synthesized from methanol by using the DME synthesis catalyst charged inside the tube on its inlet side and also synthesis heat is generated by the synthesis of DME. Next, gasoline is synthesized from the DME that flows through the reaction tubes 34 towards the outlet side by using the gasoline synthesis catalyst, and the temperature of the synthesis heat generated in the synthesis of gasoline is higher than that generated in the case of synthesis of DME. The generated gasoline is collected from the respective reaction tubes 34 into the gasoline supply line 32 to be discharged therefrom. As described above, the respective reaction tubes 34 has a temperature gradient in which the temperature gradually increases from the methanol supply line 22 toward the gasoline supply line 32.

On the other hand, the combustion air that has been preheated and supplied from the combustion air inlet line 41 to the duct 36 has the temperature of about 200° C., for example, and this combustion air first passes through the first duct 36A located on the side of the methanol supply line 22. Then the combustion air undergoes heat exchange with the respective reaction tubes 34 via the tube wall. Next, the combustion air passes through the second duct 36B located in the center portion, and then passes through the third duct 36C located on the side of the gasoline supply line 32. Because the temperature of the respective reaction tubes 34 increases from the methanol supply line 22 toward the gasoline supply line 32, the combustion air is heated so that its temperature gradually increases by the heat exchange with the reaction tubes 34. In the above-described manner, the combustion air is heated up to the temperature of about 300° C. to about 380° C.

As described above, in carrying out heat exchange between the synthesis heat generated in the synthesis of gasoline from methanol and the combustion air, the combustion air is allowed to flow through the duct 36, and thereby a large volume of combustion air can be heated under atmospheric pressure. In addition, because the combustion air flows in order from the side of the methanol supply line 22 of the reaction tubes 34 to the side of the gasoline supply line 32 during the heat exchange with the reaction tubes 34, the temperature of the reaction tubes 34 can be cooled to and maintained at a relatively low temperature ranging from 250 to 300° C., for example, on the side of the methanol supply line 22 on which the synthesis of DME is carried out, and on the side of the gasoline supply line 32, on which the synthesis of gasoline is performed, the temperature of the reaction tubes 34 can be cooled to and maintained at a relatively high temperature ranging from 380 to 450° C., for example. Further, tubes with a large diameter can be used because the catalysts are charged inside the reaction tubes 34, and thereby employment of a complex configuration for the entire gasoline synthesis column 30 can be prevented.

Note that although one gasoline synthesis column is provided in the embodiment shown in FIG. 1, the present invention is not limited to this, and thus a plurality of gasoline synthesis columns can be serially disposed. For example, in the configuration illustrated in FIG. 3, two gasoline synthesis columns 30A, 30B are disposed and the combustion air inlet line 41 and the combustion air supply line 44 are connected to the first gasoline synthesis column 30A so that heat exchange between the combustion air and the synthesis heat generated in the synthesis of gasoline is carried out, and the gasoline supply line 32 for discharging the gasoline obtained in the first gasoline synthesis column 30A is connected to the second gasoline synthesis column 30B so that heat exchange between the gasoline and the second gasoline synthesis column 30B is carried out.

In the gasoline supply line 32, a first methanol-gasoline heat exchanger 51 can be provided between the first gasoline synthesis column 30A and the second gasoline synthesis column 30B, which is configured to perform heat exchange with the methanol supply line 22 for supplying methanol, which is the material, to the first gasoline synthesis column 30A. In addition, in the gasoline supply line 32, a second methanol-gasoline heat exchanger 53 can be provided on the downstream side of the second gasoline synthesis column 30B, which is configured to perform heat exchange with the methanol supply line 22 for supplying methanol, which is the material, to the first gasoline synthesis column 30A. Note that if both the first methanol-gasoline heat exchanger 51 and the second methanol-gasoline heat exchanger 53 are provided, the first methanol-gasoline heat exchanger 51 and the second methanol-gasoline heat exchanger 53 are disposed in this order from the first gasoline synthesis column 30A in the methanol supply line 22. In addition, in the gasoline supply line 32, a steam-gasoline heat exchanger 52 can be disposed between the second gasoline synthesis column 30B and the second methanol-gasoline heat exchanger 53 where necessary.

According to the above-described configuration, combustion air is introduced from the combustion air inlet line 41 into the first gasoline synthesis column 30A first to cool the first gasoline synthesis column 30A and also obtain the heated combustion air from the combustion air supply line 44. On the other hand, the first gasoline synthesis column 30A is cooled with the combustion air but the temperature of the obtained gasoline (containing LPG which is the material and water) is still as high as about 380° C. to about 450° C., for example. This gasoline is introduced into the first methanol-gasoline heat exchanger 51 via the gasoline supply line 32 and cooled by methanol in the methanol supply line 22. Accordingly, the second gasoline synthesis column 30B can be cooled by introducing the cooled gasoline into the second gasoline synthesis column 30B via the gasoline supply line 32.

The gasoline obtained from the second gasoline synthesis column 30B has a temperature as high as about 380° C. to about 450° C. Accordingly, heat can be recovered by generating steam by introducing this gasoline into the steam-gasoline heat exchanger 52 via the gasoline supply line 32. Furthermore, heat can be recovered by heating methanol in the methanol supply line 22 by introducing this gasoline into the second methanol-gasoline heat exchanger 53 via the gasoline supply line 32. The methanol in the methanol supply line 22 is heated by the second methanol-gasoline heat exchanger 53 and the first methanol-gasoline heat exchanger 51 serially in this order up to a temperature ranging from about 250° C. to about 300° C., for example, which is the temperature suitable for supplying the methanol to the gasoline synthesis column.

As described above, by serially disposing the plurality of gasoline synthesis columns 30, the residual thermal energy remaining after the heat of reaction of the synthesis of gasoline is used for preheating the combustion air.

EXAMPLES

Simulation of heating combustion air was carried out with respect to the embodiment shown in FIG. 1. The simulation was carried out under the conditions that the methanol-based daily production was 2,500 t, and that natural gas was used for both the material and the fuel. In addition, 50% of the heat of reaction in the gasoline synthesis column was available for the heating of the combustion air, and in the waste heat recovery portion of the steam reformer, heat was recovered from the flue gas by the flue gas-steam heat exchanger until its temperature decreased to 287° C. As a result, it was possible to heat the combustion air up to 70° C. in the steam-combustion air heat exchanger first, then up to 200° C. in the flue gas-combustion air heat exchanger, and then up to 350° C. in the gasoline synthesis column. As a result, it was possible to reduce the amount of fuel for the steam reformer by 5.8% compared with the case in which the combustion air was not preheated in the gasoline synthesis column. This amount is equivalent to 1.95% of the total energy of the material and the fuel used in the system for producing gasoline from natural gas via methanol.

Figure 3:
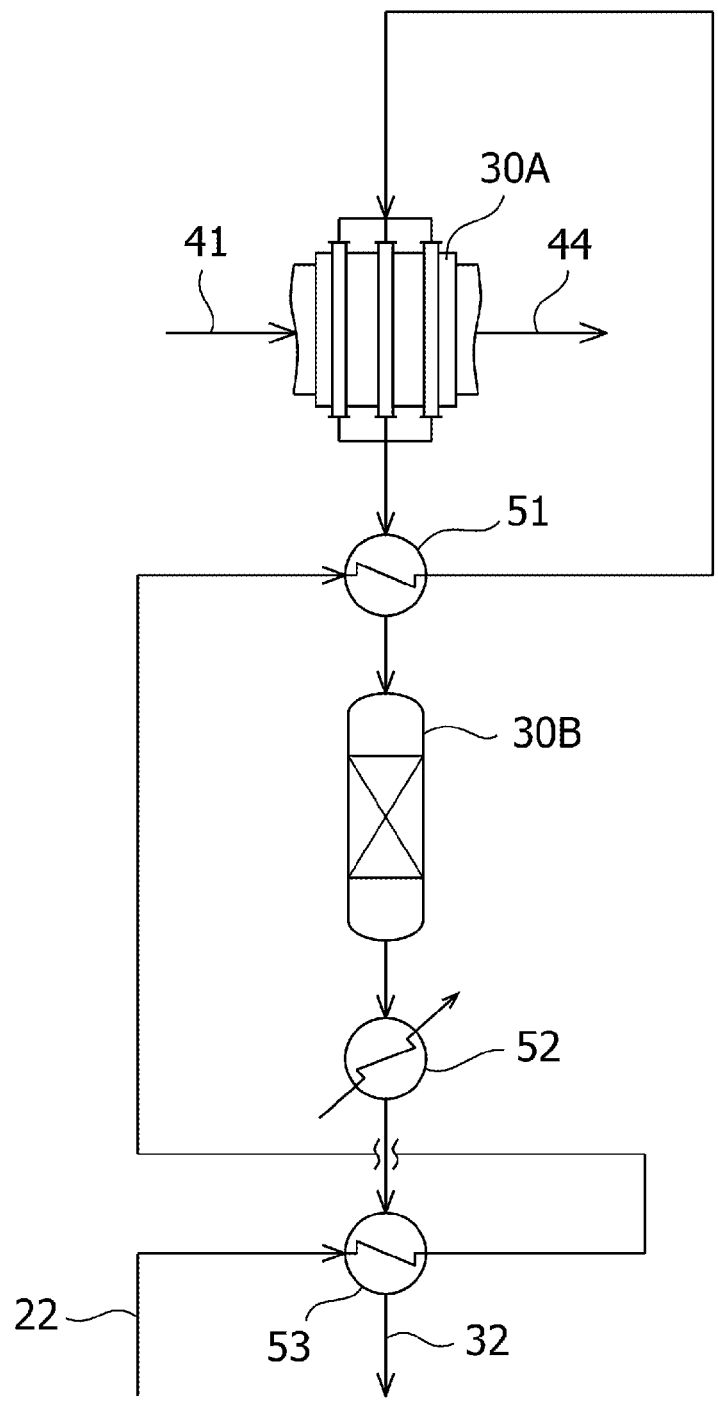
FIG. 3 is a schematic view showing another embodiment of the system according to the present invention.

Simulation of cooling two gasoline synthesis columns was carried out with respect to the embodiment shown in FIG. 3. Note that the simulation was carried out for the case in which the daily production of methanol was 2,500 t and the supplied methanol contained 18 wt. % of water. In addition, 50% of the heat of reaction in the first gasoline synthesis column was available for the heating of the combustion air. Results of the experiments are shown in Table 1, in which 200° C. combustion air at was introduced into the first gasoline synthesis column and 130° C. methanol was supplied.

TABLE 1

|  | Temperature (° C.) | | |
| --- | --- | --- | --- |
|  | Combustion air | Methanol | Gasoline |
| Inlet of first gasoline synthesis column | 200 | — | — |
| Outlet of first gasoline synthesis column | 350 | — | 420 |
| Outlet of first methanol-gasoline synthesis heat exchanger | — | 300 | 300 |
| Outlet of second gasoline synthesis column | — | — | 420 |
| Outlet of steam-gasoline heat exchanger | — | — | 250 |
| Outlet of second methanol-gasoline heat exchanger | — | 180 | 200 |

As shown in Table 1, it was possible to cool the first and the second gasoline synthesis columns to a specific temperature and maintain the temperature of the columns, and also heat can be excellently recovered from gasoline heated to a high temperature and obtained from the first and the second gasoline synthesis columns by using methanol, which is the material for the reactions run in the gasoline synthesis column.

DESCRIPTION OF REFERENCE NUMERALS

10: Steam reformer
11: Reaction tube
12: Burning portion
13: Material supply line
14: Fuel supply line
15: Waste heat recovery portion
16: Stack
17: Flue gas-steam heat exchanger
18: Reformed gas supply line
19: Reformed gas heat exchanger
20: Methanol synthesis column
22: Methanol supply line
30: Gasoline synthesis column
32: Gasoline supply line
34: Reaction tube
35: Partitioning member
36: Duct
40: Air preheating device
41: Combustion air inlet line
42: Flue gas-combustion air heat exchanger
43: Fan
44: Combustion air supply line
45: Steam-combustion air heat exchanger

The invention claimed is:

1. A system for producing gasoline from natural gas via methanol, comprising:
   a steam-reforming device for generating reformed gas by steam-reforming natural gas;
   a methanol synthesis device for synthesizing methanol from the reformed gas generated by the steam reforming device;
   a gasoline synthesis device for synthesizing gasoline from methanol synthesized by the methanol synthesis device; and
   an air preheating device for preheating combustion air to be supplied to the steam-reforming device by heat exchanging between the combustion air and synthesis heat generated in a reaction tube charged with gasoline synthesis catalyst in the gasoline synthesis device.

2. The system according to claim 1, wherein the gasoline synthesis device comprises at least two gasoline synthesis columns; and a heat exchanger for carrying out heat exchange between gasoline synthesized by a first gasoline synthesis column of the at least two gasoline synthesis columns and methanol to be supplied to the first gasoline synthesis column,
   wherein a second gasoline synthesis column of the at least two gasoline synthesis columns is cooled with gasoline cooled by the heat exchanger.

* * * * *